United States Patent [19]

Elahi

[11] 4,338,094
[45] * Jul. 6, 1982

[54] MACROENCAPSULATED IMMUNOSORBENT ASSAY TECHNIQUE

[76] Inventor: Nasik Elahi, 41-77 Frame Pl., Flushing, N.Y. 11355

[*] Notice: The portion of the term of this patent subsequent to Jul. 28, 1998, has been disclaimed.

[21] Appl. No.: 137,617

[22] Filed: Apr. 7, 1980

Related U.S. Application Data

[63] Continuation-in-part of Ser. No. 87,928, Oct. 25, 1979, Pat. No. 4,280,816.

[51] Int. Cl.$^3$ .................. G01N 33/54; G01N 33/56
[52] U.S. Cl. .................................. 23/230 B; 23/915; 23/920; 422/57; 422/58; 422/61; 424/1; 424/12; 435/7; 435/810
[58] Field of Search .................. 23/230 B; 424/12; 422/57, 58, 61

[56] References Cited

U.S. PATENT DOCUMENTS

| | | | |
|---|---|---|---|
| 3,951,748 | 4/1976 | Devlin | 424/12 X |
| 3,952,091 | 4/1976 | Grunberg | 424/12 X |
| 3,959,080 | 5/1976 | Orth | 424/12 X |
| 3,985,867 | 10/1976 | Redshaw | 424/12 X |
| 4,061,466 | 12/1977 | Sjoholm | 23/230 B |
| 4,108,972 | 8/1978 | Dreyer | 424/12 X |
| 4,131,544 | 12/1978 | Elahi | 23/230 B X |
| 4,138,474 | 2/1979 | Updike | 424/12 X |
| 4,166,102 | 8/1979 | Johnson | 424/12 X |

Primary Examiner—Sidney Marantz
Attorney, Agent, or Firm—Kenyon & Kenyon

[57] ABSTRACT

A process for the immunoassay of antigens in a biological sample wherein an element comprised of particulate supported antibody loosely encapsulated and confined within a porous filter membrane material is utilized for addition to the biological sample. The method is particularly applicable to the radioimmunoassay (RIA), enzyme-linked immunoassay (ELIA) and fluorescent immunoassay (FIA) techniques for determining the presence and concentration of minute amounts or protein antigens in biological fluid samples, and for performing multiple assays utilizing these methods.

7 Claims, No Drawings

MACROENCAPSULATED IMMUNOSORBENT ASSAY TECHNIQUE

BACKGROUND OF THE INVENTION

The present application is a continuation-in-part of my co-pending application U.S. Ser. No. 87,928, filed Oct. 25, 1979, U.S. Pat. No. 4,280,816.

This invention relates to a method for the detection of the presence and concentration of compounds in a liquid medium and, in particular, to an improvement in immunoassay techniques for determining the presence and concentration of protein antigens, such as drugs, hormones and the like in a liquid sample.

The art has long recognized the need for analytical methods and apparatus for determining the presence of a particular compound or class of compounds in a liquid medium, and a variety of techniques has been developed to accomplish this aim. Particularly important areas for such methodology lie in the field of medicine wherein, for example, information regarding the presence of a particular compound in a patient is utilized as a diagnostic tool for determining various physical conditions or abnormalities. Methods for analyzing blood or urine samples for the presence of glucose, cholesterol or urea are well-known examples of these techniques.

Much of the general utility of methods for determining merely the presence of particular compounds in a liquid system, e.g., a biological fluid, is limited where accurate quantitative analysis of minute amounts or concentrations of the compound in the fluid is required. Accordingly, techniques have also been developed for achieving this aim. Such techniques include those known as radioimmunoassay (RIA), enzyme-linked immunoassay (EIA or ELIA) and fluorescent immunoassay (FIA), having particular applicability in the determination of the concentration of drugs or hormones in a biological fluid either in connection with treatment of a patient or in the field of forensic medicine.

The RIA, ELIA and FIA techniques utilize anitbodies developed specifically for a particular compound (antigen) whose presence is to be determined. The antibody reacts with (i.e., becomes bound to) only its specific antigen and, hence, displays the specificity required for accurate quantitative determinations. In practice, the antibody prepared against, for example, amphetamine, is added to a serum sample to be analyzed. Additionally, a known quantity of amphetamine which has been labelled (i.e., coupled to a signal emitter such as radioactive tritium for the RIA technique, an enzyme-linkage whose presence can be determined spectrophotometrically for the ELIA technique or a fluorescently identifiable compound for the FIA technique) is also added to the sample. Competitive and/or non-competitive displacement then takes place over a period of time wherein both the labelled antigen and the antigen to be determined, present in the sample fluid, compete for attachment to the antibody. A material is then added which will quantitatively remove all antigen from the sample which has not been bound to antibody. The remaining fluid, containing the antibody and any bound antigen, is then transferred to an appropriate device (e.g., a scintillation counter, spectrophotometer or a fluorescence indicator) for determining the presence of labelled antigen therein. The quantity of labelled antigen found is a measure of the amount of unlabelled antigen in the biological sample tested. Thus, for example, if the sample contained no antigen, all the labelled antigen originally added to the sample would be removed with the antibody as would be indicated by a radiation count or optical density equal to that obtained from the known quantity of labelled antigen added to the sample at the beginning of the test. Alternatively, a determination that less than the original amount of labelled antigen now appears with the antibody indicates that antigen was present in the sample in an amount correlatable to the decreased amount of labelled antigen found with the antibody. In an alternative procedure, after the above-noted competitive attachment between labelled and unlabelled antigen has taken place, the antibody is removed from the liquid system by protein precipitation and it, rather than remaining fluid, is analyzed by the appropriate method to determine the amount of labelled antigen thereon.

Variations of the RIA, ELIA and FIA techniques exist where the antibody is added to the sample already in the form of a complex with its labelled antigen. The same methods as above-described are then utilized to determine the quantity of labelled antigen, if any, displaced from the antibody as an indication of the presence of unlabelled antigen in the sample.

A recent advance in the field of RIA is described in papers authored by L. Wide, et al., appearing at Journal of Immunochemistry, 4, 381 (1967); Biochim. Biophys. Acta. 130, 257 (1966); and Acta Endochrinol., 63, Suppl. 142, 207 (1970). According to this method, radioimmunosorbentassay (RISA), the antibody and its labelled antigen are complexed or affixed to a solid support material, e.g., CNBr-activated Sephadex. This complex is then added to the fluid sample to be tested in the manner as above-described. This method provides an improved means for separating the antibody from the sample after the competitive displacement has occurred, e.g., the solid support material containing antibody, labelled antigen and antigen from the sample, if any, can simply be removed in toto from the test vial. This material, or the fluid remaining after removal of the supported material from the sample, can then be tested for its radioactivity to determine the quantity of antigen present in the original sample.

A parallel advance in the ELIA technique was first described in the work of Catt and Tregear, "SCIENCE", 158, 1570 (1967) and further elucidated by van Weeman and Schuurs, "Immunochemistry", 21,667 (1975) and Engvall and Jonsson, "Biochem. Et Biophysica Acta", 251, 427 (1971). In this method, enzyme-linked immunosorbentassay (ELISA), the antibody is coupled to a solid immunosorbent, for example, Sepharose. The immunosorbent is then incubated in a solution containing the enzyme-linked antigen and the sample to be analyzed. The antigen conjugated to an appropriate enzyme is analogous to the radio-labelled antigen in the RIA technique. As with all immunoassays, a competitive binding of the antigen tagged with the enzyme and the antigen present in the sample takes place with the antibody. After the appropriate incubation period, the immunisorbent is removed. The fluid, containing the remaining free enzyme-linked antigen is then reacted with a suitable color developer, for example, o-phenylaniline diamine and hydrogen peroxide solution to produce a colorimetric reaction for reading optical densities in a spectrophotometer.

A similar advance also exists for the FIA (fluorescent immunoassay) technique, described in the work of Burgett, M. W., et al., Journal of Immunological Methods, 16 211 (1977); Burgett. M. W. et al., Clinical Chimica Acta 78 277 (1977); and Comoglio A. Massaglia E., Rollerei E. and Roia, U. Biochimical Biophysica Acta 420; 246-257 (1976). In this methodology (which can be termed FISA), the antibody to individual human immunoglobulins, namely IgG, IgA, IgM, etc., is first covalently coupled to polyacrylamide beads. A sufficient amount of the immunsorbent thus formed is then incubated with the sample to be analyzed, so that all the immunoglobulin present in the unknown sample is bound to the solid immunosorbent. The immunosorbent-immunoglobulin complex is next treated with a fluorescently-coupled-mono-specific antiserum. In this step, the amount of the fluorescently labelled antiserum attached to the immunosorbent is directly proportional to the amount of the particular immunoglobulin present in the sample. The unreacted materials are washed and centrifuged and the complex is broken by glycine treatment to release the bound fluorescent-antibody for fluorometric determination.

Although the RIA, ELIA and FIA techniques and the recent advancements therein provide a highly accurate, quantitative determination for specific antigens, a major disadvantage resides in the inability to conveniently test for the presence of more than one antigen at any one time. Thus, it is not presently possible to determine, for example, the quantitative presence of the common classes of drugs—amphetamines, barbiturates and opiates—in one test since there is no means for distinguishing the particular antibodies to which these drugs would report. One recent attempt in this regard is reported by Cleeland, et al., Clinical Chemistry, 22/6, 712-725 (1976) wherein a triple assay test for the three above-mentioned drugs is described. In this method, the three labelled antigens and their antibodies are mixed and contacted with a single biological fluid sample. However, the test is only effective in determining the complete absence of any of the drugs. Any positive indication of drug presence cannot distinguish which particular drug or drugs are contained in the sample. Hence, where a positive indication is found, the three assays must then be performed individually to determine exactly which drug or drugs caused the positive response.

A very definite need exists, therefore, for a method for immunoassay determinations capable of performing multiple assays to detect, in one test, the quantitative presence of more than one antigen.

SUMMARY OF THE INVENTION

An object of the present invention is the provision of a process for facilitating the immunoassay of antigens in a biological fluid.

A further object of the invention is the provision of a process for the immunoassay of one or more antigens in a biological fluid in a single procedure.

These and other objects are achieved by a process for the immunoassay of a antigen in a biological fluid sample wherein the antibody for the antigen is contained on a particulate solid support material and wherein the supported antibody particulates are loosely encapsulated and confined within a rigid, porous filter membrane having a pore size less than the size of the particulates.

In accordance with the process of the invention, testing elements, comprised of the antibody-containing solid support particulates loosely encapsulated within the porous filter membrane material can be prepared for each specific antigen whose presence is sought to be determined, i.e., each element contains a differenet antibody. The nature of the elements permit their easy identification, e.g., by color-coding or size differential, so that the elements, when removed from the biological sample, can be distinguished from each other to obtain quantitative measurement for each antigen. Thus, for example, an element containing particulate support material coupled with the antibody specific to amphetamines, a similar element with the antibody for barbiturates and a similar element with the antibody for opiates can be prepared and coded and added to the same biological fluid sample. In accordance with standard immunoassay methodology, these elements can then be removed and separately tested for radioactivity or spectrophotometrically assayed to arrive at quantitative determinations for the three drugs.

The process according to this invention may be practiced in a number of ways. Thus, for example, in one embodiment, antibody can be complexed (e.g., sorbed) onto the particulate solid support material, the particulates then loosely encapulated in the rigid porous filter membrane, and the capsule element added to a biological sample containing labelled antigen. Alternatively, the particulate solid support material may have complexed theron both the antibody and its labelled antigen prior to encapsulation and addition to a biological fluid.

In these embodiments, the complexing of antibody to the particulate solid support material may be accomplished by first loosely encapsulating the particulate solid support within the rigid porous filter membrane and then bringing the so-formed element into contact with a solution of antibody to sorb the antibody thereon. This encapsulated antibody/support element may than be added to a biological fluid sample containing added labelled antigen, or the element may first be contacted with labelled antigen to affix the labelled antigen to the supported antibody in the element prior to addition of the element to the sample to be tested.

The process of the present invention is described in further detail hereinafter. However, it is noted that the encapsulation technique of the present invention is described in considerable detail in my U.S. Pat. No. 4,131,544, issued Dec. 26, 1978. Since the subject matter of that patent relates to important features of the present invention, the patent is incorporated by reference herein. An abstract referring to initial findings in connection with the process and product of my above identified patent was presented at the Tenth International Congress of Clinical Chemistry, Mexico City, February-March 1978.

DETAILED DESCRIPTION OF THE INVENTION

The various embodiments of the present invention are hereinafter described with reference to the immunoassay of drugs, such as amphetamines, barbiturates and opiates, in a sample of biological fluid such as urine or blood serum. However, it will be appreciated that the process is broadly applicable to any analytical determination which can be made by immunoassay technique such as RIA, RISA, ELIA, ELISA, FIA and FISA. Thus, for example, the process of this invention can be utilized to determine the concentration of antigens other than the noted drugs, such as, for example, pharmaceutical preparations or their active componenets or metabolites, hormones, enzymes or other proteins in biological fluids such as human or animal serum, blood, plasma, urine, bile, etc.

The particular details regarding the origins and theory of radioimmunoassay, enzyme-linked immunoassay and flourescent immunoassay techniques are well known and the source of extensive literature. As will be appreciated, the present invention does not critically depend upon the choice of various reagents, labelling compounds, solid supports, detection apparatus and other like conditions and materials known to the art for use in general in immunoassay methods.

According to one embodiment of the present invention, a supported antibody is prepared by affixing the antibody to a particulate solid support material. The support material may be a simple sorbent, such as powdered talc, magnesium silicate, kaolin, Quoso (silica microgranules), florisil or cellulose powder wherein antibody can be sorbed thereon; other physical adsorbents, such as polytetrafluoroethylene-g-amino-styrene, Protapol powder, Protapol DI-1, acrylamide gel, bentonite particles, bromoacetylcellulose, beaded agarose, benzacryl AA, polyacrylamide beads, glass beads and the like; or a material to which antibody may be linked through a covalent bonding, e.g., Sepharose and Sephadex (Bio-Rad Corporation). In addition, the supported antibody can be prepared without a foreign solid support material per se, i.e., wherein the antibody itself is polymerized or cross-linked with ethylchloroformate or glutaraldehyde to form solid, particulate antibody particles.

In the foregoing examples, the antibody or antiserum for the drug whose concentration is to be measured is contacted with the particulate solid support material (where utilized) to form supported antibody particulates by co-valent linking, adsorption at alkaline pH, simple adsorption, etc. The preparation and isolation of the particular antiserums for the desired drug or antigen is well-known in the art and is not described in detail here.

The particulates, being antibody per se or containing antibody sorbed or affixed thereon, are then loosely encapsulated in a rigid, porous filter membrane material in a manner shown in my U.S. Pat. No. 4,131,544. Thus, a desired quantity of particulates is placed in a porous filter membrane which may be fashioned from, e.g., Teflon, polypropylene, polyethylene, gelatin, cellulose esters, nitrocellulose membranes and like materials. The pore size of the filter membrane material is chosen such that it will retain within its confines the particulates therein, yet be large enough to permit contact of the particulates with the fluid into which the element or capsule is placed.

The rigidity required of the capsule or element in order to provide a fixed volume in which the particulates may freely agitate may be supplied by the porous filter membrane material per se or through the use of a skeletal support means (e.g., perpendicular, circular ribs) around which the filter membrane material may be formed. The porous filter membrane material can be physically fused, ultrasonically welded, or welded using other methods which do not generate excessive heat which might destroy the antibody, to effect permanent closure and provide the loose encapsulation of particulates.

A sample of biological fluid to be analyzed is placed in a appropriate vial or test tube along with suitable buffers and a quantity of the drug for which analysis is required labelled with a radio emitter such as tritium or some other suitable material, or an enzyme-linkage. To this sample mixture is added the element or capsule containing the particulate supported antibody. The contents are then gently rotated for a sufficient time to permit the competitive binding between labelled and unlabelled drugs to occur. The liquid contents of the vial are then poured out and the capsule element submitted to an appropriate detection device, for example, for determining radioactivity emitted by any labelled drug therein. The amount of labelled drug so found is then correlated to the concentration of drug present in the original fluid sample utilizing well known techniques in the immunoassay field. Alternatively, the liquid contents can be measured for the presence of labelled drug therein.

In an alternate embodiment of the present invention, the particulate solid support material containing antibody can be contacted with labelled drug in order to couple or bind the drug to the antibody present on the particulates. These particulates are then encapsulated as described and the capsule added to a biological fluid without, of course, the addition of labelled drug. After displacement of labelled drug from the antibody, the capsule is removed and either it or the remaining fluid submitted to appropriate detection means for the labelled drug.

In each of the described embodiments the particulate solid support material can first be loosely encapsulated within the rigid porous filter membrane prior to its treatment with the antiserum solution. In this embodiment, heat-sealing means to effect closure of the filter membrane to form a capsule is permissible. Thus, the capsule can simply be placed in a vial with the antibody solution to sorb or affix the latter to the support. The so-fashioned capsule may then be further contacted with labelled antigen to bind the labelled antigen to the supported antibody in the capsule. The capsule is then added to a biological fluid sample. Alternatively, the capsule containing supported antibody particulates can be added to a mixture of labelled antigen and biological fluid sample to be analyzed.

Where binding of antibody to support material requires preliminary treatment of the support with an activating material (e.g., CNBr in the case of Sephadex), the activating material can be brought into contact with the particulate support either before or after the support is encapsulated.

Although the process of the present invention provides a simple efficient means for the immunoassay of a single compound in a biological fluid, its most beneficial result resides in its ability to provide a means for determining multiple assays, e.g., testing a biological sample for the quantitative presence of more than one compound. Thus, separate capsules containing particulate supported antibody for a particular antigen can be prepared and color-coded or marked in a manner such that they can be simultaneously added to a single biological fluid sample and each removed after suitable incubation time (which may vary among the capsules based upon the particular compound being tested for) and subjected to means for detecting the labelled antigen thereon.

The process of the present invention may be practiced utilizing any suitable apparatus for receiving the fluid components involved in the test procedure and the capsule elements containing particulate supported antigen. Preferred vessels for carrying out the procedure, however, are described in my U.S. Pat. No. 4,131,544.

The following examples are provided to illustrate the process of the present invention as applied to the multiple immunoassay for amphetamines, barbiturates and opiates.

EXAMPLE I

Coarse Sephadex G-25 particles (particle size ranging from 100 to 300 microns) are immersed in a vessel containing 40 ml per gram of particles of a 25% solution of CNBr in distilled water. The pH is maintained at 10.5 by addition of 4 M NaOh. After 30 minutes, the polymeric particles are thoroughly washed with distilled water, followed by acetone washing, and stored at $-20°$ C.

Globulin fractions of the particular antiserums or antibodies for amphetamines, for barbiturates and for opiates are separately prepared by precipitation with 15% $Na_2SO_4$. 0.1 ml of each globulin fraction is diluted to 0.5 ml with 0.1 M $NaHCO_3$ and each fraction then separately treated with 100 mg. of the Sephadex particles. After contact for 24 hours, the polymer particles are washed thoroughly with 0.1 M $NaHCO_3$ and 0.1 M Acetate buffer (pH 4), and shaken in a blender with assay buffer (0.2% BSA in phosphate buffered saline pH 7.5 containing 0.05% sodium axide and 0.05% Tween-20).

Sheets of Teflon TFE macrofiltration material (Spectramesh, manufactured by Spectrum Medical Industries, Los Angeles, Calif.), having a mesh size of $74\mu$, are cut into 1 cm. square strips. Each piece is placed in the hollow well of differently-sized metallic dies and stamped with precision-fitting die stampers. The mesh material assumes a rigid, semispherical shape of 4.5, 5 and 5.5 mm. diameter, with no damage to the pore size. 5 mg. (or an amount sufficient to bind 20–50% antigen in 24 hours; average 40% binding required) are placed inside one semisphere which is then mated with another hollow half of the die fitted with an empty semisphere of mesh material, and the two halves bonded ultrasonically. Each capsule is then color-coded for each particular antibody to provide a means to facilitate identification in addition to the size differential.

The final form of the capsules containing particulate supported antigen provides a sufficient void volume for the free agitation of the particulate therein and maximum surface contact with the liquid phase.

For assay, 0.25 ml of the sample to be investigated, 0.1 ml each of solution with the labelled drugs and 2 ml of the assay buffer are placed in the pressurizing syringe device of the type described in my U.S. Pat. No. 4,131,544 modified to provide a stopcock at the bottom thereof. The appropriate number of immunosorbent capsules, one for each category of the drugs are placed in the mixture and the contents sealed with the locking clip on the syringe plunger to yield slight positive pressure. As an additional precaution, the polypropylene syringe can be siliconised to make it still more inert. The contents are gently rotated for a time sufficient to insure the optional incubation at the appropriate temperature. The assay fluid is poured out by opening the stopcock. Alternatively, if there is a considerable difference in the incubation period of the different components, then the capsules can be selectively removed and washed serially with 1 ml, followed by 3×2.5 ml of 0.5% Tween-20 in 0.15 M NaCl and counted.

EXAMPLE II

Two 3-gms aliquots of cyanogen bromide activated Sepharose-4B is treated with 1 mM HCL for 15 minutes, washed in 0.1 M sodium bicarbonate (pH 9.5), allowed to stand for 1 hour. The excess bicarbonate is removed. The activated Sepharose aiquots are separately treated with 1 ml solution of the particular antibodies, e.g., immunoglobulin G (IgG) and progesterone. The contents are agitated for the length of time appropriate to effect coupling of the CNBr-activated Sepharose 4B with antibodies. The contents are allowed to stand to further deactivate the Sepharose surface and encapsulated in the same manner as described in Example I.

The enzyme-labelled antigens are prepared in the following manner:

For progesterone the enzyme-labelling is effected by coupling 11-alpha-hydroxy progesterone-11-hemi succinate to horseradish peroxidase (RZ 3.0) by a modified mixed anhydride technique at $-20°$ C. for 1 hour and then $0°$ C. for 1 hour.

The purified labelled antigen is obtained by gel exclusion chromatography on Sephadex G-25 and yields a ratio of 6.5:1 moles of the enzyme per moel of antigen.

For IgG, the conjugation between the enzyme, alkaline phosphatase and the IgG antigen is made by glutardialdehyde. 0.1 ml of the clear suspension of the enzyme solution is added to 0.1 ml of a solution containing 0.5 mg pure rabbit IgG. The mixture has a IgG-alkaline phosphatase ratio of 1:3 and dialyzed overnight against phosphate buffered saline. The contents are then reacted with 10 ul of 4.2% glutardialdehyde in phosphate buffered saline for 2 hours. The mixture is diluted to 1 ml with buffered saline, dialyzed overnight and separated on a Spharose 6B column in 0.05 M Tris-HCL buffer (pH 8.0). The eluted enzyme-labelled antigen is stabilized with 5% human serum albumin and stored at $4°$ C. with 0.2% $NaN_3$.

For assay, are added 0.5 ml each of sample and appropriate buffers, 0.1 ml of IgG labelled alkaline phosphatase and 0.1 ml of progestrone-11-alpha-hemi succinyl-horseradish peroxidase solution in a test-tube or the preferred syringe embodiment as described in my U.S. Pat. No. 4,131,544. The contents are shaked gently. The incubation for progesterone assay is approximately 40 minutes while the optimal requirement for the IgG assay is 16 hours. The capsules are selectively retreived and thoroughly washed.

After retreival, each capsule contains the Sepharose-antibody-enzyme-labelled antigen complex. In order to obtain multiple specific assays, what is required is to effect the release of the enzyme-labeled antigen from the complex in a buffered solution so it can be coupled to color developers. This can be accomplished by either very gentle heating ($55°$ C.) or elution in low pH (approximately 1.0–2.0 ) and high salt solutions.

The released enzyme-labeled antigen is next reacted with appropriate color couplers. For IgG the color is developed by adding 1 ml of 0.05 M sodium carbonate (pH 9.8) containing 1 mg/ml solution of p-nitro-phenyl phosphate and 1 mM magnesium chloride. The color reaction is stopped by adding 0.1 ml of 1 M sodium hydroxide and read in a spectrophotometer for optical density.

For progesterone, the color is developed using a o-phenylene diamine/hydrogen peroxide. The addition of 4 N sulphuric acid stops the reaction and the fluid can be read in a spectrophotometer at 492 nm.

The present invention is also obviously applicable, as noted earlier, to immunoassay techniques involving non-competitive displacement. Thus, for example, as in the earlier-described methodology, supported antibody is provided as an element comprising particulate supported antibody loosely encapsulated and confined within a rigid porous filter membrane having a pore size less than the size of the particulates, the element being of a substantially fixed, predetermined volume such that the particulates freely agitate therein. The supported antibody element(s) is then contacted with a liquid medium, containing the antigen to be determined and for which the supported antibody is specific, in amounts and for a time sufficient to bind all the antigen to its supported antibody. Antibody specific to the antigen and which has been labelled to permit its detection, is then brought into contact with the supported antibody element thereto. The labelled antibody will itself then bind or attach to the antigen which is bound, on another site, to the supported antibody (i.e, the "bonding" or coupling is supported antibody-antigen-antibody) in proportion to the quantity of antigen present on the supported antibody. Since the supported antibody was added in an amount and for a time sufficient to bind all antigen in the original liquid medium, the amount of labelled antibody which binds to the antigen (bound to the supported antibody) is thus correlatable to the amount of antigen originally present in the sample liquid medium. Thus, for example, a known quantity of labelled antibody may be added and, after allowing sufficient time for binding with the antigen bound to the supported antibody, either the quantity of "free" (unbound) labelled antibody remaining in the medium or the amount of labelled antibody bound or complexed to the antigen, can be determined and correlated to the quantity of bound antigen.

As will be apparent, the earlier extensive discussion regarding the supported antibody element per se, with respect, for example, to the means and methods for providing the element and the materials used therefor, applies equally to the embodiment of the invention above-described, which differs from the earlier discussed methodologies only in providing for antibody, rather than antigen, labelling and non-competitive, rather than competitive, binding of antigen to the supported antibody element.

The following example illustrates the foregoing embodiment as applied to FIA.

EXAMPLE III 400 mgms of Bio-gel polyacrylamide beads, #P-300, 50-100 wet mesh, (Bio-Rad Laboratories, Richmond, Calif.) is washed 10 times with water and treated overnight at 4° C. with a 6% solution of glutaraldehyde in 0.1 M-Phosphate buffered saline (PBS), pH 7.0. The beads activated with glutaraldehyde are washed fifteen times with water and are ready for bonding with the immunoglobulin antiserums.

Separate aliquots of Goat antiserums for immunoglobulins IgA, IgG and IgM are prepared in the amounts of 5.4 mg in 10 ml of phosphate buffered saline containing 0.1 M-phosphate and 0.14 M-Sodium chloride, pH 7.4. Each globulin aliquot is incubated with 10 ml solution of the activated beads at room temperature for 48 hours to effect covalent coupling of the activated beads and the globulin antiserum. The immunosorbent thus formed is washed with phosphate buffered saline and any remaining active sites are blocked by suspension in 0.1 M TRIS buffer, pH 7.4 for 18 hours at room temperature. The aliquots are next washed 10 times with PBS, twice with 50 ml of 0.2 M glycine hydrochloride, pH 2.8 and 50 ml of 0.2 M potassium phosphate dibasic, followed by washing with PBS and water and lypholized.

Sheets of Spectramesh macrofiltration material woven for either teflon, polypropylene, polyethylene or nylon (Spectramesh Spectrum Medical Industries, Los Angeles Calif.) having a mesh size of approximately 250 microns, are cut into 1 cm square strips. Each piece is placed in the hollow well of differently sized metallic dies and stamped with precision fitting stampers. The spectramesh material assumes a rigid shape corresponding to 4.5, 5 and 5.5 mm diameter with no damage to pore size.

5 mg each of the immunosorbent (or an amount sufficient to bind all the antigen) is placed inside one semisphere which is then mated with another hollow half of the die fitted with an empty semisphere of mesh material and the two halves are cemented together. Each capsule may also be color-coded for each antibody, as a ready means of identification, in addition to the size differential.

The final form of the capsules containing the particulate supported antigen provides a sufficient void volume for the free agitation of the particulates therein and offers maximum surface contact with the liquid phase.

For assay, 10 $\mu$l of the sample to be analyzed, 5 ml of phosphate buffer pH 7.5, containing 0.15 M-NaCl and 0.01-M phosphate and three capsules, each corresponding to immunosorbents corresponding to IgG, IgA and IgM, are placed in the pressurizing syringe device of the type described in my U.S. Pat. No. 4,131,544. The contents are sealed with the locking clip on the syringe plunger to provide slight positive pressure. The contents are gently rotated for a time sufficient to insure optimal incubation at 37° C. The contents are depressurized and 50 ul solutions each of fluorescein-isothiocyanate-conjugated goat or rabbit antihuman antibodies, specific for IgG, IgA and IgM, are added. Incubation at 37° C. for at least one hour with gentle rotation is then performed. All fluids are discarded and the capsules are washed 10 times with phosphate buffered saline.

Each capsule is placed in a separate borosilicate test tube and treated twice with 2 ml washing of glycine-hydrochloride 0.2 M, pH 2.8 and one washing with 1 ml of 0.2 M glycine-hydrochloride, pH 2.2. The volumes of the glycine treatment solution can be adjusted accordingly to yield optimal volumes for the subsequent assay. The glycine treatment also has the effect of breaking up the fluorescein-antibody complex on the immunosorbent and provides a clear fluid aliquot for fluorometric determinations at the excitation wavelength of 293 and fluroescence at 520. Using the encapsulated technique all three principal immunoglobulin fractions, IgM, IgA and IgG can be quantitated after only one incubation of sample to yield specific results for each component.

What is claimed is:

1. In a method for determining the presence and concentration of an antigen in a liquid medium by immunoassay wherein a supported antibody to said antigen is brought into contact with said liquid medium in an amount and for a time sufficient to bind substantially all of said antigen to said supported antibody, and wherein antibody to said antigen which has been labelled to permit its detection is contacted with the supported antibody to which antigen has been bound so as to bring about binding of the labelled antibody to the antigen bound to the supported antibody, and thereafter determining by suitable detection means the amount of the labelled antibody either bound to said antigen bound to said supported antibody or the amount of the labelled antibody which is not bound to said antigen, the improvement comprising providing said supported antibody as an element comprising particulate supported antibody loosely encapsulated and confined within a rigid porous filter membrane having a pore size less than the size of said particulates, said element being of a substantially fixed, predetermined volume such that said particulates agitate freely within said element.

2. The method of claim 1 wherein said supported antibody comprises antibody bound to a solid particulate support material.

3. The method of claim 2 wherein said element is prepared by bringing said element containing particulate support material into contact with a solution containing said antibody for a time sufficient to sorb said antibody onto said particulate support material.

4. The method of claim 1 wherein said antibody labelled to permit its detection is antibody labelled with a fluorescent compound.

5. A method for determining the presence and concentration of at least two different antigens in a single liquid medium comprising:
   (a) providing a first element comprising particulate, supported antibody to a first antigen loosely encapsulated and confined within a rigid porous filter membrane having a pore size less than the size of said particulates, said first element being of a substantially fixed, pre-determined volume such that said particulates agitate freely within said element;
   (b) providing a second element comprising particulate, supported antibody to a second antigen which is different from said first antigen, loosely encapsulated and confined within a rigid porous filter membrane having a pore size less than the size of said particulates, said second element being of a substantially fixed, predetermined volume such that said particulates agitate freely within said element;
   (c) providing on each of said first and second elements means for differentiating therebetween;
   (d) simultaneously bringing each of said first and second elements into contact with said liquid medium for a time sufficient to permit the entire content of said first and second antigens in said medium to bind to their respective antibodies within said first and second elements thereby forming first and second antibody-antigen complexes;
   (e) thereafter simultaneously bringing each of said first and second elements into contact with a liquid medium containing first and second antibodies, each labelled to permit detection thereof, and capable of binding to their respective first and second antibody-antigen complexes formed in step (d) for a time sufficient to permit said binding;
   (f) removing said first and second elements from said liquid medium; and
   (g) subjecting each of said first and second elements to suitable means for detecting the amount of labelled antibody bound to the antibody-antigen complexes therein.

6. The method according to claim 5 wherein said supported antibodies comprise polymerized antibodies containing no foreign support material.

7. The method according to claim 1 wherein said supported antibody comprises polymerized antibody containing no foreign support material.

* * * * *